(12) United States Patent
Palmaz

(10) Patent No.: US 7,235,098 B2
(45) Date of Patent: Jun. 26, 2007

(54) MEDICAL DEVICES HAVING MEMS FUNCTIONALITY AND METHODS OF MAKING SAME

(75) Inventor: Julio C. Palmaz, San Antonio, TX (US)

(73) Assignee: Advanced Bio Prosthetic Surfaces, Ltd., San Antonio, TX (US)

( * ) Notice: Subject to any disclaimer, the term of this patent is extended or adjusted under 35 U.S.C. 154(b) by 27 days.

(21) Appl. No.: 10/945,203

(22) Filed: Sep. 20, 2004

(65) Prior Publication Data

US 2005/0177223 A1    Aug. 11, 2005

(51) Int. Cl.
*A61F 2/06* (2006.01)
(52) U.S. Cl. .................................... 623/1.15
(58) Field of Classification Search ............ 623/1.15, 623/1.16, 1.18, 1.44, 1.46, 1.49; 606/191–198; 604/93.01, 191
See application file for complete search history.

(56) References Cited

U.S. PATENT DOCUMENTS

| | | | |
|---|---|---|---|
| 5,903,099 A | 5/1999 | Johnson et al. | 313/495 |
| 6,004,441 A | 12/1999 | Fujiwara et al. | 202/412 |
| 6,051,422 A | 4/2000 | Kovacs et al. | 435/287.1 |
| 6,201,980 B1 | 3/2001 | Darrow et al. | 600/347 |
| 6,293,966 B1 | 9/2001 | Frantzen | 623/1.15 |
| 6,296,615 B1 | 10/2001 | Brockway et al. | 600/486 |
| 6,442,413 B1 | 8/2002 | Silver | 600/345 |
| 6,486,588 B2 | 11/2002 | Doron et al. | 310/322 |
| 6,656,162 B2 * | 12/2003 | Santini et al. | 623/1.42 |
| 2001/0026111 A1 | 10/2001 | Doran et al. | 310/322 |
| 2002/0125208 A1 | 9/2002 | Christenson et al. | 216/2 |
| 2003/0040791 A1 | 2/2003 | Oktay | 623/1.17 |
| 2003/0059640 A1 | 3/2003 | Marton et al. | 428/544 |

FOREIGN PATENT DOCUMENTS

WO    WO 04/035122    4/2004

OTHER PUBLICATIONS

"A Surface-Tension Driven Micropump for Low-Voltage and Low-Power Operations" by Yun, K.S., et al., *J. Microelectromechanical Sys.*, vol. 11, No. 5, pp. 445-461 (Oct. 2002).

"Singe Mask, Large Force, and Large Displacement Electrostatic Linear Inchworm Motors" by Yeh, R., et al., *J. Microelectromechanical Sys.*, vol. 11, No. 4, pp. 330-336 (Aug. 2002).

(Continued)

*Primary Examiner*—Kevin T. Truong
(74) *Attorney, Agent, or Firm*—Rosenbaum & Associates, PC; David G. Rosenbaum; Sreenivasarao Vepachedu

(57) ABSTRACT

Implantable medical devices, including stents, grafts, covered stents, catheters, patches or the like having regions of the device which are functionalized employing microelectromechanical systems that are capable of acting as electromechanical sensors or biosensors in response to either an endogenous event, such as tissue growth, biochemical binding events, pressure changes, or respond to an externally applied stimulus, such as RF energy, to cause a change in the state of the device, such as to induce an oscillation signal which may be interrogated and interpreted external the body or may generate an induced electrical or electromagnetic potential in the device to activate micromotors to effect a geometric change in the device.

13 Claims, 15 Drawing Sheets

OTHER PUBLICATIONS

"Wireless Data Blaster" by Leeper, D.G., Scientific American.com, pp. 1-3 (May 2002).

"Measuring Electrical Materials Properties Using Microfabricated Interidigated Microsensor Electrodes (IMEs) and Independently Addressable Microband Electrodes (IAMEs)," by Guiseppi-Elie, A., *An ABTECH Application Note*, http://www.abtechsci.com/pdfs/resist0501.pdf, pp. 1-3 (May 2001).

"Sub-10 $cm^3$ Interferometric Accelerometer with Nano-g Resolution" by Loh, N.C., et al., *J. Microelectromechanical Sys.*, vol. 11, No. 3, pp. 182-187 (Jun. 2002).

"An Artificial Taste Sensor Based On Conducting Polymers" by Riul, Jr., A., et al., *Biosensors and Bioeelctronics*, pp. 1-5 (2003).

"Bio-smart Hydrogels: Co-joined Molecular Recognition and Signal Transduction in Biosensor Fabrication and Drug Delivery" by Brahim, S., et al., *Biosensors and Bioelectronics*, vol. 17, pp. 973-981 (2002).

"Ga-filled Single-Crystalline MgO Nanotube: Wide-temperature Range Nanothermometer" by Li, Y.B., et al. *Applied Physics Letters*, vol. 83, No. 5, pp. 999-1001 (Aug. 4, 2003).

"A Biosensor that uses Ion-channel Switches," by Cornell, B.A., et al., *Letters to Nature*, pp. 580-583 (1997).

"Effects of Direct Current Electric Fields on Cell Migration and Actin Filament Distribution in Bovine Vascular Endothelial Cells" by Li, X., et al., *J.Vasc. Res.*, vol. 39, pp. 391-404 (2002).

"Electronic Detection of Bio-Species on a Chip" by Li, H., et al., http://www.nnf.cornell.edu/2002cnfra/2002cnfra54.pdf, pp. 54-55 (2002).

Abstract: "Dielectrophoretic Separation and Manipulation of Live and Heat-Treated Cells of *Listeria* on Microfabricated Devices with Interdigitated Electrodes" by Li, H., *J. Sensors and Actuators*, (Apr. 2002).

"Microelectromechanical Systems: Advanced Materials and Fabrication Methods, Chapter 2, 3 and 4" by The National Academy of Sciences, http://www.nap.edu/openbook/0309059801/html/14.html, pp. 14-37 (1997).

* cited by examiner

| Specificity | Basic Approach |
|---|---|
| Low | Impedance Spectroscopy |
| High | Enzyme-Substrate Interaction |
| Higher | Receptor/Ion-channel Complex |

MEDICAL DEVICES HAVING MEMS FUNCTIONALITY AND METHODS OF MAKING SAME

BACKGROUND OF THE INVENTION

The present invention relates generally to the field of medical devices suitable for in vivo use, such as implantable devices, indwelling devices, catheters and delivery systems. More particularly, the present invention relates to implantable medical devices, such as endoluminal stents, that are capable of acting as sensors and/or actuators in vivo.

With the advent of microelectromechanical system (MEMs) technology, manufacture of very small scale devices has become feasible. The principal application of MEMs technology has, heretofore, been in the electromechanical arts, in particular fluidics and fluid sensors. The present invention, however, adapts MEMs technology to the field of medical devices and, in particular, to the field of implantable medical devices that are designed to sense in vivo conditions, alter the geometry of the device, and/or deliver metered doses of bioactive substances in vivo.

The field of implantable MEMs based medical devices has extended to diagnostic microsystems, including miniature mass spectrometers, molecular-recognition biosensors, and microfluidic processors, surgical Microsystems, such as microsensors and micromotors, and therapeutic Microsystems, such as implantable and transdermal drug delivery Microsystems. Such types of microdevices are described in Polla, D. L., et al., "Microdevices in Medicine," *Ann. Rev. Biomed. Eng.* 2000, 02:551–576, which is hereby incorporated by reference. Further description of implantable medical sensors is found in U.S. Pat. No. 6,201,980, which is hereby incorporated by reference. Further description of a microactuator for controlled drug delivery may be found at Low, L. M., et al., "Microactuators toward microvalves for responsive controlled drug delivery," *Sensors and Actuator*, B 678 (2000) 149–160, which is also hereby incorporated by reference.

Micropumps, high resolution microaccelerometers, and electrostatic linear motors are examples of micro-scale electromechanical machines that rely upon low-voltage and low power consumption requirements. See, e.g., Yun, K. S., et al., "A Surface-Tension Driven Micropump for Low-voltage and Low-Power Operations," *J. Microelectromechanical Sys.*, 11:5, October 2002, 454–461, Yeh, R., et al., "Single Mask, Large Force, and Large Displacement Electrostatic Linear Inchworm Motors," *J. Microelectromechanical Sys.*, 11:4, August 2002, 330–336, and Loh, N. C., et al., "Sub-10 $cm^3$ Interferometric Accelerometer with Nano-g Resolution," *J. Microelectromechanical Sys.*, 11:3, June 2002, 182–187, each of which is hereby incorporated by reference.

Conducting polymers have been used as sensors for the development of electronic tongues by fabricating nanostructured films for use as individual sensing units. The films operate by impedance spectroscopy for signal transduction in the frequency range of 1–1 MHz to detect trace amounts of tastants and inorganic contaminants in liquid systems. Riul, Jr., A., et al., "An Artificial Taste Sensor Based On Conducting Polymers," *Biosensors and Bioelectronics*, 00 (2003) 1–5, which is hereby incorporated by reference. In a related vein, hydrogels and conducting polymers have been combined as an electroactive hydrogel composite that traps enzymes within the composite matrix for biosensor construction and chemically stimulated controlled release. Glucose, cholesterol and glactose amperometric biosensors have been made using this composite material that display extended linear response ranges between $10^{-5}$ to $10^{-2}$ M with response times of less than sixty seconds. pH sensors were made by cross-linking the hydrogel component with dimethylaminoethyl methacrylate monomer. See, Brahim, S., et al., "Bio-smart Hydrogels: Co-joined Molecular Recognition and Signal Transduction in Biosensor Fabrication and Drug Delivery," *Biosensors and Bioelectronics*, 17 (2003) 973–981, which is hereby incorporated by reference.

Single crystalline MgO nanotubes filed with Gallium have been used as wide-temperature range nanothermometers. See, e.g., Li, Y. B., et al. "Ga-filled Single-Crystalline MgO Nanotube: Wide-temperature Range Nanothermometer," *App. Phys. Let.*, 83:5, August 2003, 999–1001, which is hereby incorporated by reference.

It has been recognized that ion-channel switches may be used in biosensors and the current flux generated by ion's passing through the ion channel may serve as a basis for sensing a given condition. For example, an ion-channel switch has been made of a lipid membrane containing gramicidin ion channels linked to antibodies and tethered to a gold electrode. This tethered membrane creates an ionic reservoir between the gold electrode and the membrane which is electrically accessed through connection to the gold electrode. In the presence of an applied potential, ions flow between the reservoir and the external solution when the channels are conductive. When the ion current is switched off, mobile channels diffusing within the outer half of the membrane become crosslinked to the antibodies and immobilized. See, Cornell, B. A., et al., "A Biosensor that uses Ion-channel Switches," Letters to Nature, 1997.

Finally, it is now known that electrical fields effect endothelial cell migration. See, Li, X., et al., "Effects of Direct Current Electric Fields on Cell Migration and Actin Filament Distribution in Bovine Vascular Endothelial Cells," *J. Vasc. Res.*, 2002; 39:391–404, which is hereby incorporated by reference. Controlling endothelial cell migration is a significant step toward designing implantable devices that exhibit greater healing responses. Thus, by designing implantable devices that employ controlled electrical fields, endothelial cells will be more susceptible to binding to the device and propagating along the device surfaces to promote rapid and complete healing and minimize smooth muscle cell proliferation or thrombogenic effects.

In order to design implantable devices having controlled electrical fields, advantageous use may be made of inter-digitated electrodes to create a galvanotactic medical device. Interdigitated electrodes have been employed in dielectrophoresis to separate live and heat-treated *Listeria innocua* cells on microfabricated devices employing interdigitated electrodes by utilizing the difference in dielectric properties between the alive and dead cells, Li, H., et al., at http://www.nnf.cornell.edu/2002cnfra/2002cnfra54.pdf and Li, H., "Dielectrophoretic Separation and Manipulation of Live and Heat-Treated Cells of *Listeria* on Microfabricated Devices with Interdigitated Electrodes," *J. Sensors and Actuators*, Apr. 2002 which are hereby incorporated by reference. Interdigitated microsensor electrodes, also called interdigitated arrays are microfabricated from patterns of noble metals deposited on an insulating substrate chip. These devices are designed for simultaneous interrogation of electrical, electrochemical or optical properties of polymeric films and coatings in microelectrochemistry and electrical/electrochemical impedance spectroscopy. See, e.g., Guiseppi-Elie, A., "Measuring Electrical Materials Properties Using Microfabricated Interdigitated microsensor Electrodes (IMEs) and Independently Addressable Microband Electrodes (IAMEs)," An ABTECH Application Note, http://www.abtechsci.com/pdfs/resist0501.pdf, May 2001, which is hereby incorporated by reference.

SUMMARY OF THE INVENTION

The present invention provides several embodiments of stent-based or graft-based sensors and actuators. In accordance with a first embodiment of the invention there is provided a galvanotactic stent in which the stent material is at least partially fabricated by multi-layer physical vapor deposition. A first substrate layer is deposited, then a conductive layer is deposited and interdigitated electrodes formed in the conductive layer, with adjacent electrodes being separated by dielectric material, a final top insulating layer is deposited and a plurality of openings formed and patterned to match the position of the interdigitated electrodes in the intermediate conductive layer. Upon application of an electrical current to the device, the interdigitated electrodes become charged and a focused current emanates from the openings in the top insulating layer and is patterned in correspondence with the pattern of openings in the top layer.

Suitable power sources may include an externally applied RF source that induces resonator circuitry in the stent to charge a solid state capacitor formed in the stent, thus providing an integrated power supply within the stent to maintain a charge source for the interdigitated electrodes. Alternative power sources include, without limitation, externally applied electromagnetic fields, ultrasound, UV or photoemissive energy, or thermal energy.

Since it is known that endothelial cells migrate under the influence of an applied field, the presence of an electrical field integral with the stent is expected to enhance endothelialization of the stent surfaces and promote the formation of healthy neointimal tissue, while lowering the incidence of restenosis associated with stent implantation.

It is also contemplated in accordance with the present invention that an endoluminal stent may include a conductive polymer with a biological element that forms an embedded circuit in the stent that responds to changes in a physiological condition in the body and produces a change in conductivity in known relationship with the change in the physiological condition. Examples of this type of mechanism of action are conductive polymers such as polypyroles and polypyrolidones used as artificial tongues in the food industry.

Another aspect of the invention is that conductive polymers on a stent may be used to bind oxidases and generate peroxides to yield free electrons and provide a source of electrical current for the sensor device on the stent. Alternatively, voltage generated by ion channel activity from receptor binding mediated events may be employed to generate a voltage for a stent-based sensor.

For each of the types of inventive microsensor devices contemplated by the present invention, it is necessary to have an external means for interrogating the microsensor device to determine its state. Transcutaneously applied RF energy is preferably employed to interrogate the inventive microsensor devices, or cause the inventive microsensor devices to actuate for either drug delivery or micromachine actuation. There is an exponential relationship between frequency and data density that may be transmitted over a given frequency is known in the art. Similarly, there is an inverse relationship between frequency and range. See, e.g., Leeper, D. G., Scientific American, May 2002, which is hereby incorporated by reference. In the ultrawideband frequency, large gigabyte level data densities may be obtained, but over relatively short distances of a few meters. It is contemplated that in the present invention, at terahertz frequencies it is expected that higher data densities may be obtained even while sacrificing range. Since a range of only a few centimeters is required to transcutaneously interrogate an implanted medical device, very high frequencies in the terahertz range may be employed with the concomitant effect of yielding terabyte data densities that are expected to yield sufficient data streams to construct real-time 3D images representative of the condition of the implanted microsensor medical device.

DETAILED DESCRIPTION OF THE PREFERRED EMBODIMENTS

Figure 1:
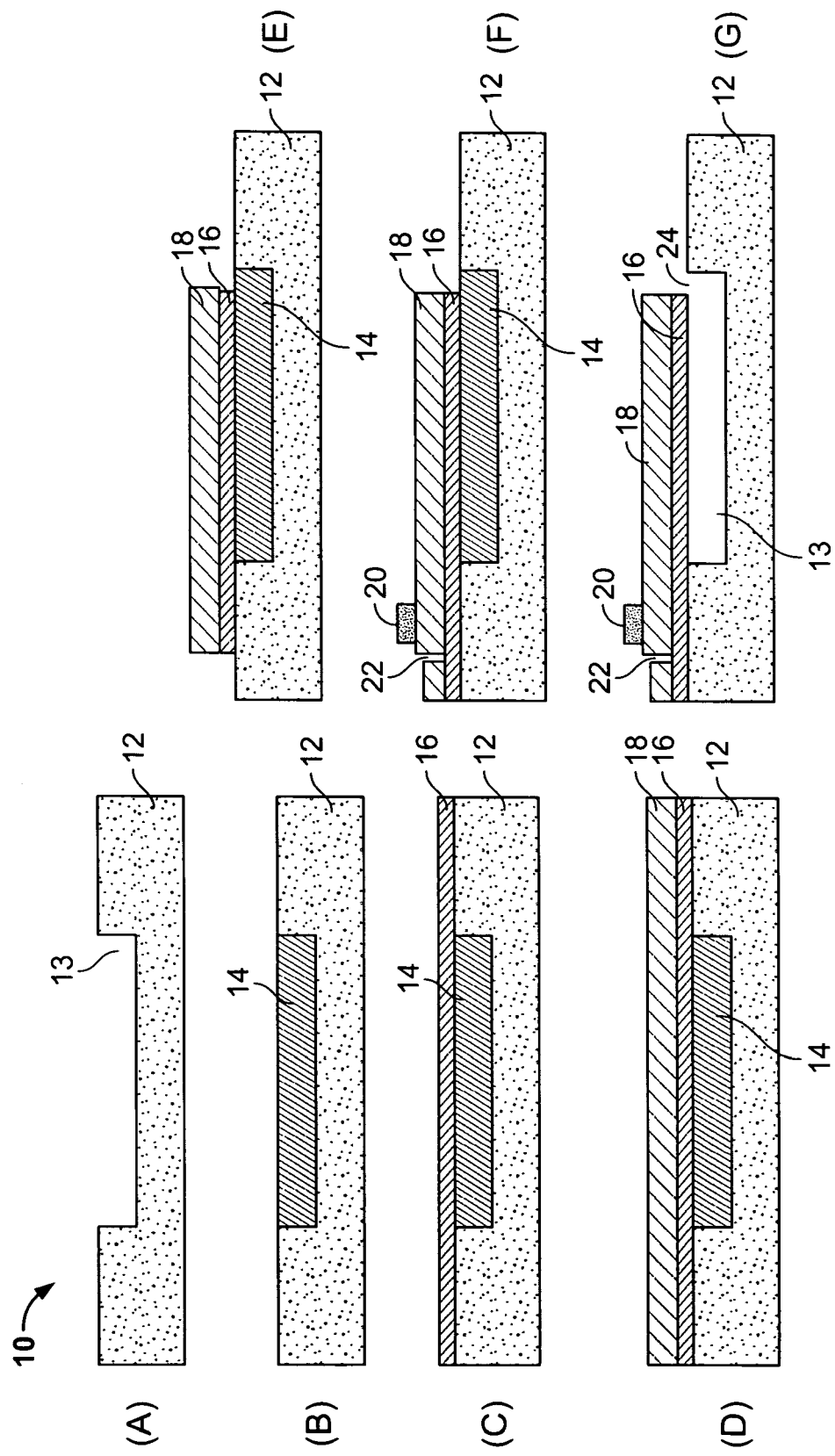
FIG. 1 is a sequential diagram with panels A–G illustrating fabrication of a cantilever structure in a MEMs device.

The accompanying FIGS. 1–18 depict different aspects of the present invention, including physical vapor deposition and formation of microcantilevers for use a microsensors or as drug delivery fluidic pumps, an exemplary variably resonant circuit with communicating interrogator circuits outside the body and a passive resonator sensor circuit implanted in the body, a graph depicting the relationship between RF frequency, special capacity and range, a nanothermometer, basic elements of an interactive implantable stent, a lateral accelerometer fabricated using MEMs technology, a diagrammatic galvanotactic device for generating a field gradient for imparting endothelial cell migration, a microcantilever based sensor for detection of thrombus formation and tissue thickness, a microcantilever based sensor for detection of molecular species based upon binding events, a table of different contemplated approaches to electronic biosensing, an diagrammatic device made of composite films of conductive polymers and lipids for impedance spectroscopy, a system for amperometric measurement by peroxide generation, an antibody/ion-channel switch as a biosensor, a drug release valve actuated by electro corrosion, a drug release valve by an artificial muscle, a micropump, sequential figures illustrating movement of a linear micromotor employing interdigitated elements and a corresponding track for relative movement of the interdigitated elements along the track (FIGS. 17A–17D), and an actuating stent having linear micromotors and tracts forming actuating ring units for purpose of radially expanding the stent in response to an applied current to the linear micromotor.

In accordance with each preferred embodiment of the invention, it is contemplated that an implantable medical device, such as a stent, stent-graft, covered stent, graft, or other similar device is fabricated in such a manner as to accommodate a MEMs device either as a discrete component coupled to the medical device, but preferably, the medical device is fabricated using physical vapor techniques as described in co-pending application Ser. No. 10/211,489 filed Aug. 2, 2002, published as U.S. Published Application US 2003/0059640 on Mar. 27, 2003, which is hereby incorporated by reference in its entirety.

It is contemplated that during fabrication of the inventive medical device, the MEMs sensors and/or actuators of the present invention will be formed during fabrication of the device and be an integral component of the device. For purposes of illustration only, reference will be made to an endoluminal stent having a plurality of structural members, with the MEMs sensors and/or actuators being described as being associated with at least one of the plurality of structural members. Those of ordinary skill in the art, however, will understand that a wide variety of medical devices are contemplated by the present invention and may serve as the carrier substrate for the MEMs sensors and/or actuators of the present invention, including, without limitation, patches, grafts, catheters, balloons, filters, coils, covered stents, or the like.

A first embodiment 10 of the present invention is illustrated with reference to FIG. 1. The structural member of the stent 12 is formed with at least one recess 13. The at least one recess is filled with a sacrificial material 14, and a microcantilever layer 16 is formed on the structural member 12 and covering the sacrificial material 14. Optionally, a piezoelectric material 18 may be provided covering the microcantilever layer 16. The piezoelectric material 18 and the microcantilever layer 16 are partially removed to form a length of the microcantilever layer 16 and piezoelectric material 18 which corresponds to the desired length of microcantilever 16, with a portion of the sacrificial material 14 now being exposed. A contact 20 and space between an adjacent cantilever 22 may be provided. Removal of the sacrificial material 14 from beneath the cantilever 16 reopens recess 13 and leaves a space 24 between a terminus of the cantilever and a terminus of the recess in which the cantilever may freely oscillate.

Figure 8:
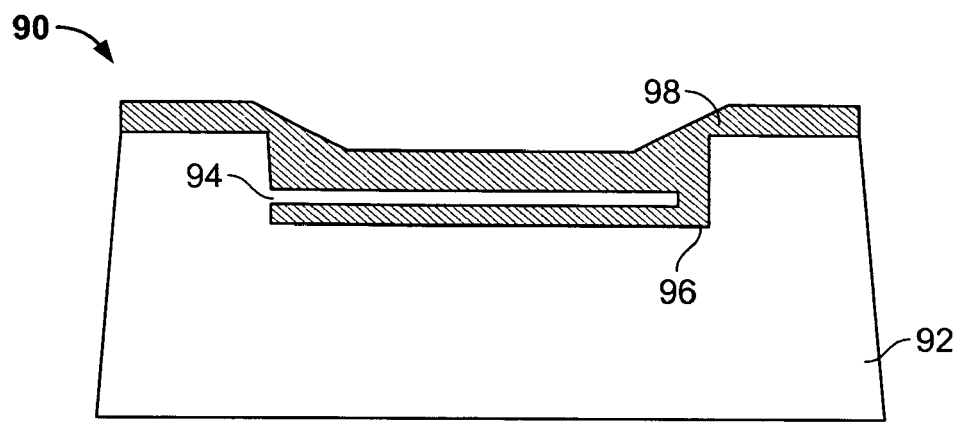
FIG. 8 is a diagrammatic elevational view of a cantilever structure of the MEMs functionalized medical device with dampening due to tissue growth around the cantilever structure.
Figure 9:
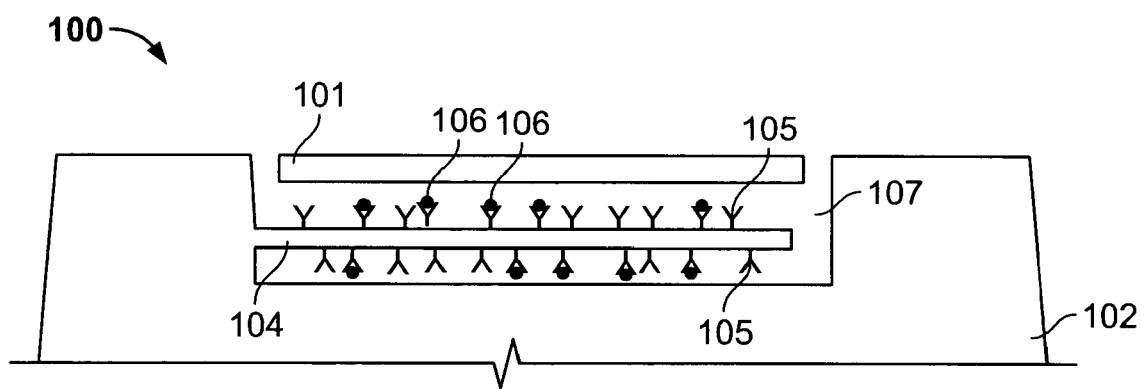
FIG. 9 is a diagrammatic elevational view of an embodiment of the cantilever structure of the MEMs functionalized medical device of the present invention for physiochemical affinity binding of biochemical species.

As illustrated in FIGS. 8–9, alternative embodiments 90 and 100 of the microcantilever concept may be used to sense thrombus 98 or vascular tissue binding to the respective medical device 92, 102, in embodiment 90, or physiochemical binding of sub-cellular components such as antibodies 105, DNA, antisense DNA or the like, to the cantilever member 94, 104, which attenuates the ability of the associated microcantilever 94, 104 to oscillate upon application of an external signal, which, therefore, returns an altered signal indicative of the condition of the device. Similarly, the microcantilevers may be used as a gate to open or close an aperture for purposes of drug delivery and may be stimulated to open or close in response either to an applied external RF signal or a binding event of an endogenous or exogenous substance.

Figure 2A:
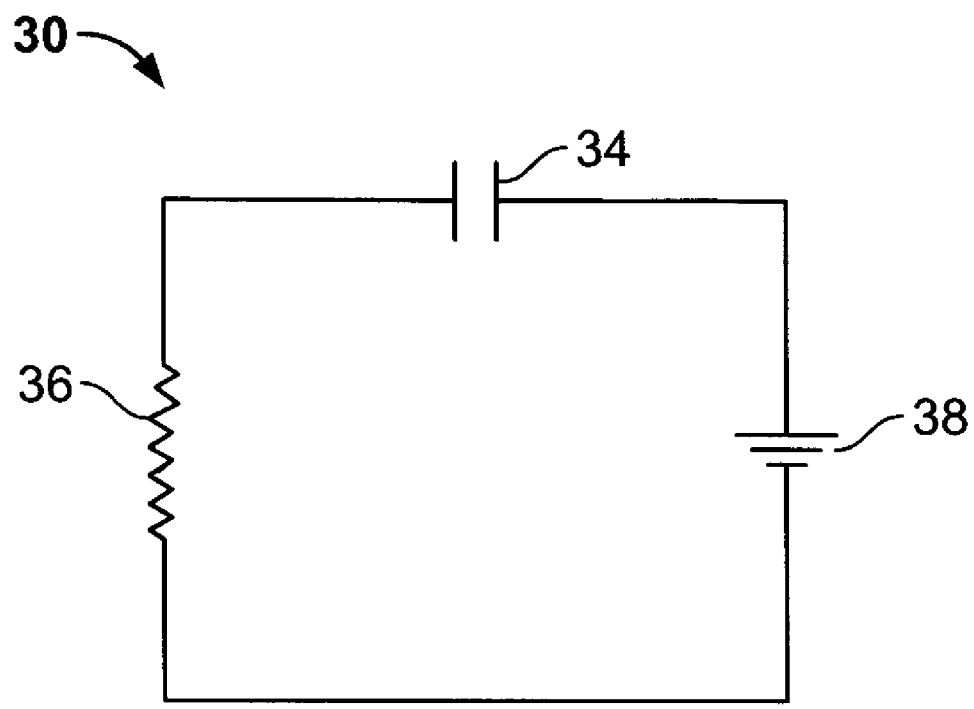
FIG. 2A is a circuit diagram depicting an interrogator circuit for generating a first electronic signal.
Figure 2B:
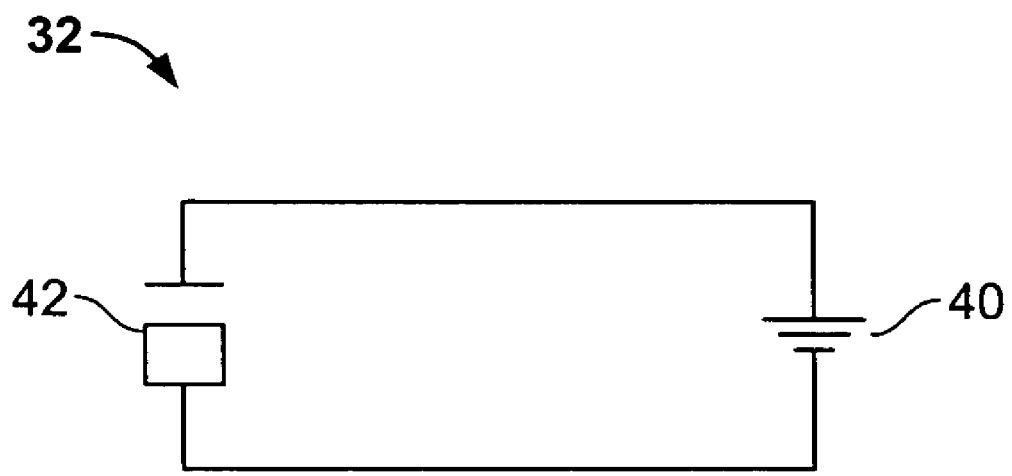
FIG. 2B is a circuit diagram depicting a passive resonator circuit for sensing the first electronic signal and activating a variable capacitor.

A sample resonant circuit having an ex vivo interrogator circuit 30 and an in vivo passive resonator circuit 32 is illustrated in FIGS. 2A and 2B. The interrogator circuit 30 consists generally of a closed loop circuit having an oscillator 34, a resistor 36 and a power supply 38, while the resonator circuit 32 consists generally of a loop circuit having a power supply 40 and a variable capacitor 42.

Figure 3:
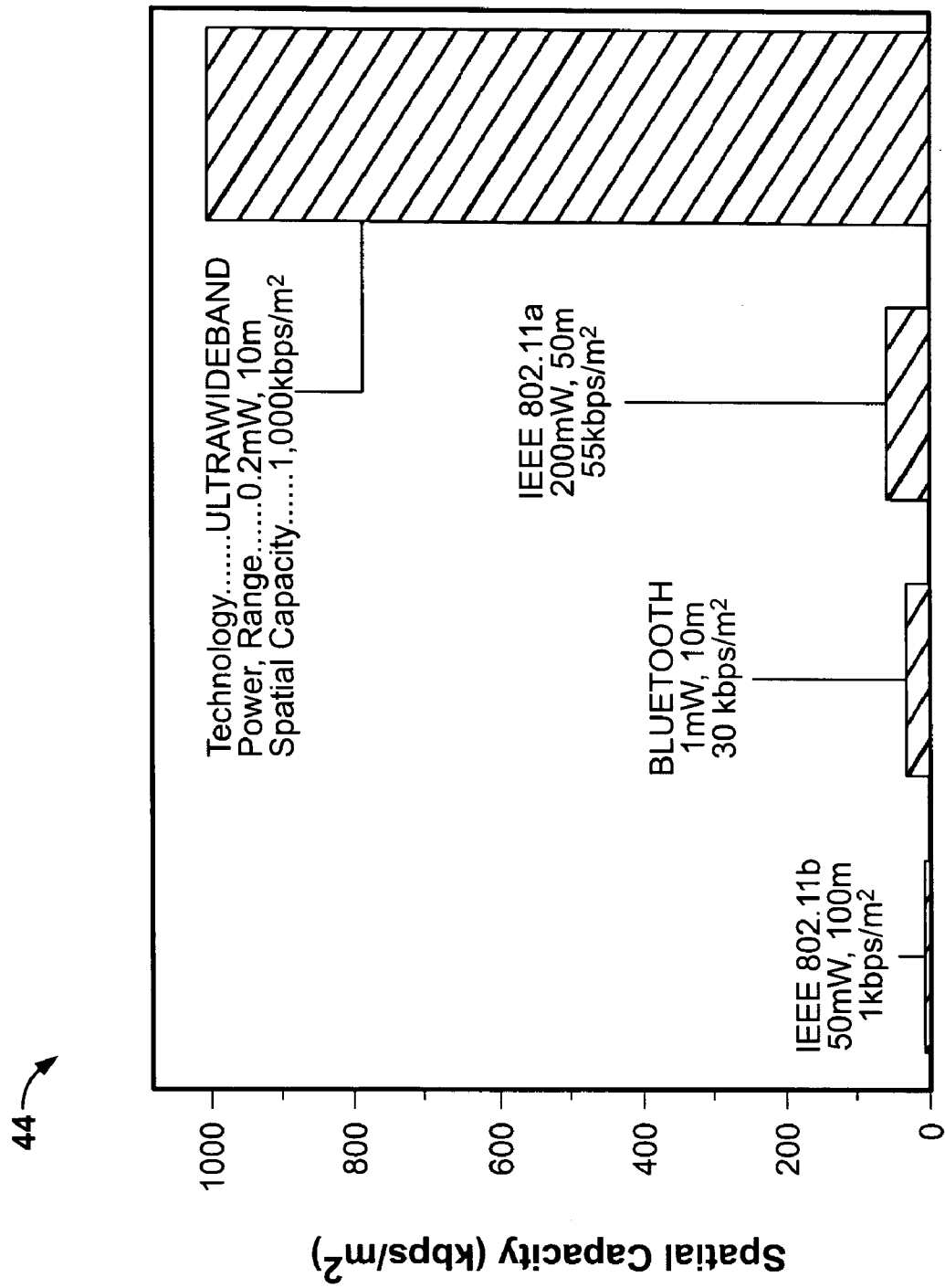
FIG. 3 is a graph illustrating the relationship between spatial capacity of different bandwidths of conventional wireless communication modalities.

As illustrated in FIG. 3, a significant relationship exists between communication frequency and spatial capacity of the bandwidth. Similarly, an inverse relationship exists between range of signal and spatial capacity. Thus, for the inventive medical application, it is desirable to employ ultrawideband frequencies which have a spatial capacity in excel of 1,000 kbps/m$^2$ and a range of 10 meters which is more than sufficient for medical applications.

Figure 4:
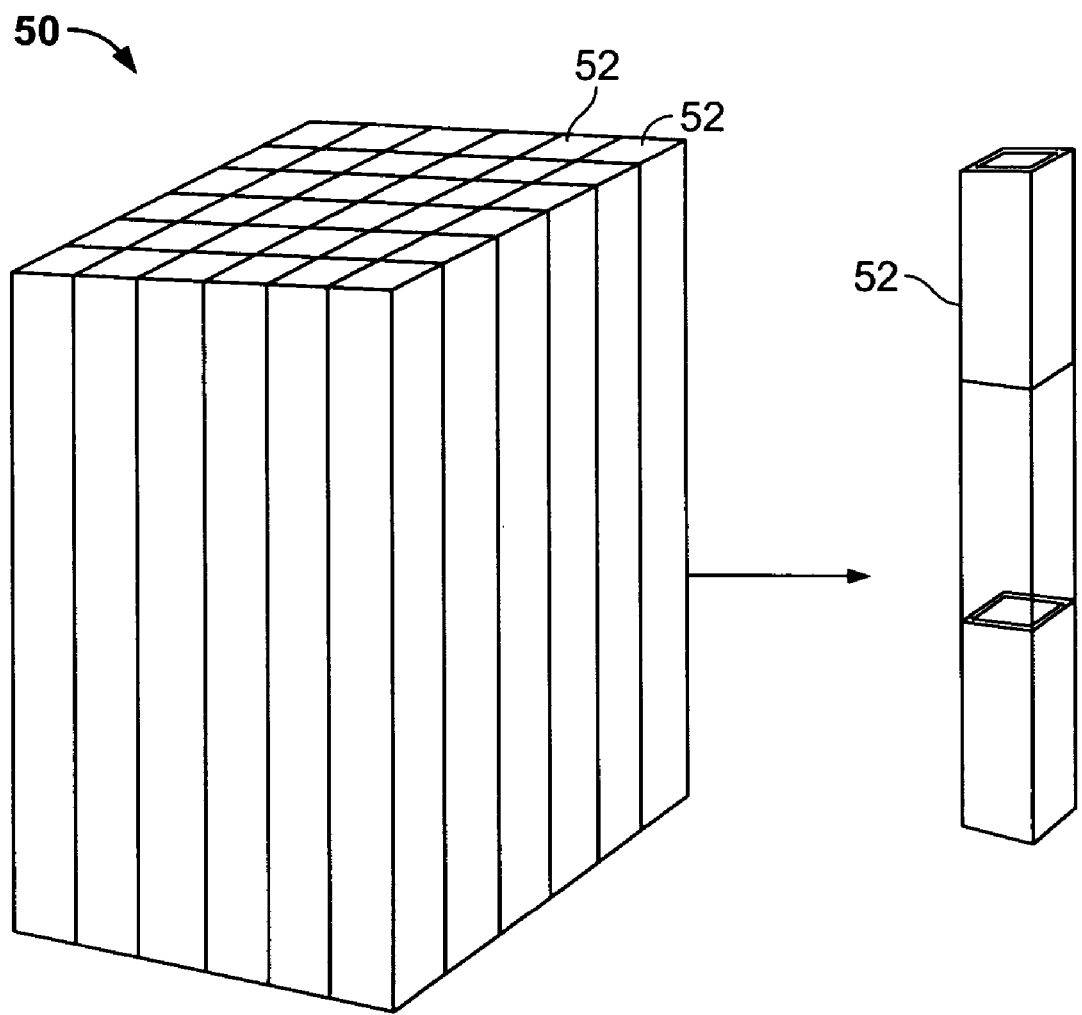
FIG. 4 is a perspective view of a nanothermometer construct useful with the inventive medical device of the present invention.

FIG. 4 depicts a nanothermometer which may be incorporated into or associated with the structural elements of a medical device. The nanothermometer consists of an array of gallium filled single crystal MgO tubules 52.

Figure 5:
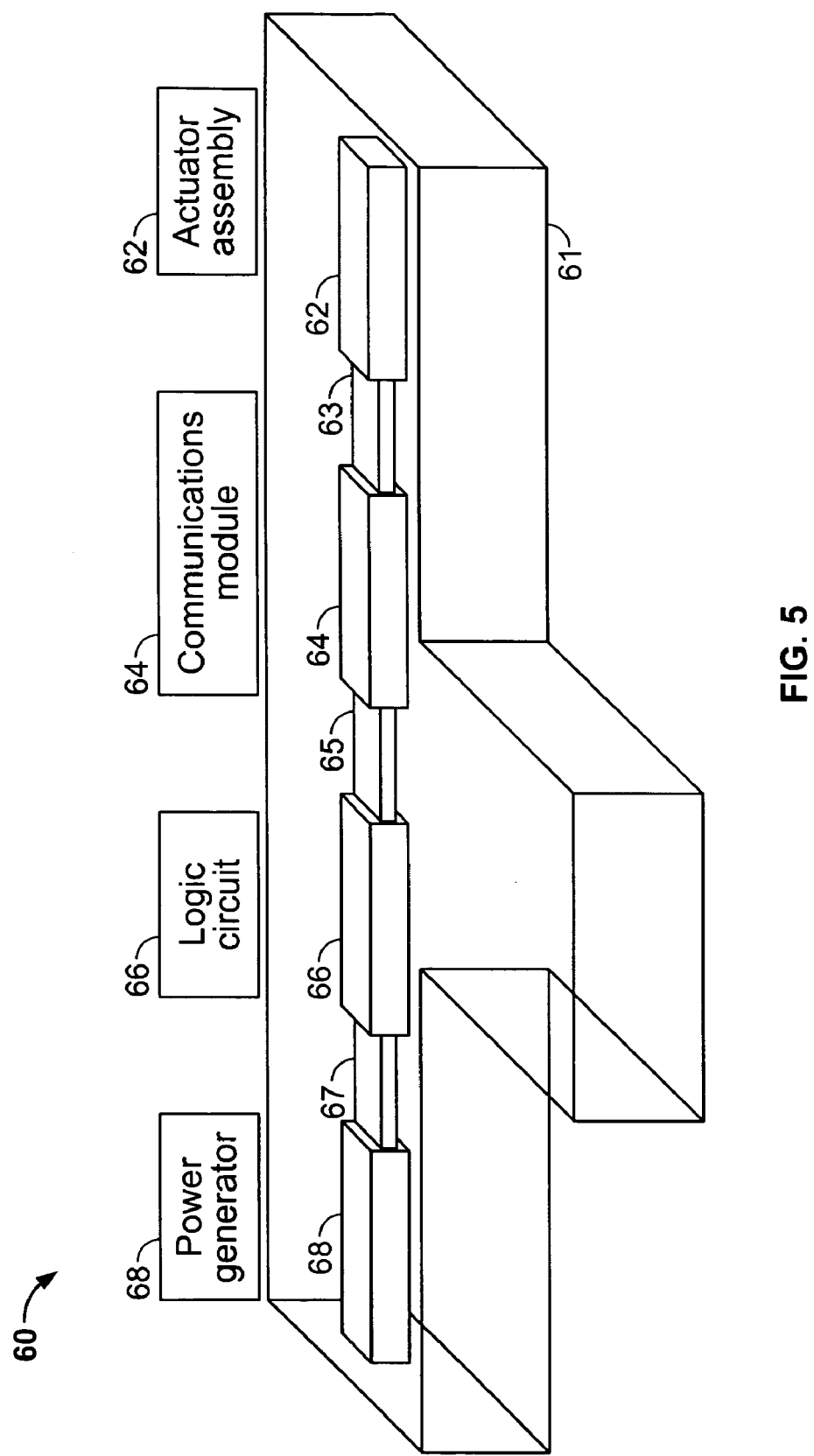
FIG. 5 is a diagrammatic view depicting the fundamental elements of the inventive functional medical device and their interactions.

FIG. 5 depicts an overview of an actuating system 60 for actuating relative movement of component parts in a medical device, such as a stent. The general components of the system are a power generator 68 coupled to logic control circuitry 66, which is, in turn coupled to a communications module 64, which communicates with actuator assemblies 62 associated with the component parts of the medical device. Thus, relative movement of the component parts relative to one another is controlled by the logic circuit 66, and overseen by the communications module 64. Interconnections 67, 65, 63 may be electrical, RF, electromagnetic, magnetic or such other functional interconnections as is known in the art. It is regarded as within the skill of the artisan to design and program the specific implements of the logic circuit 66 and the communications module 64 without the exercise of undue experimentation.

Figure 6:
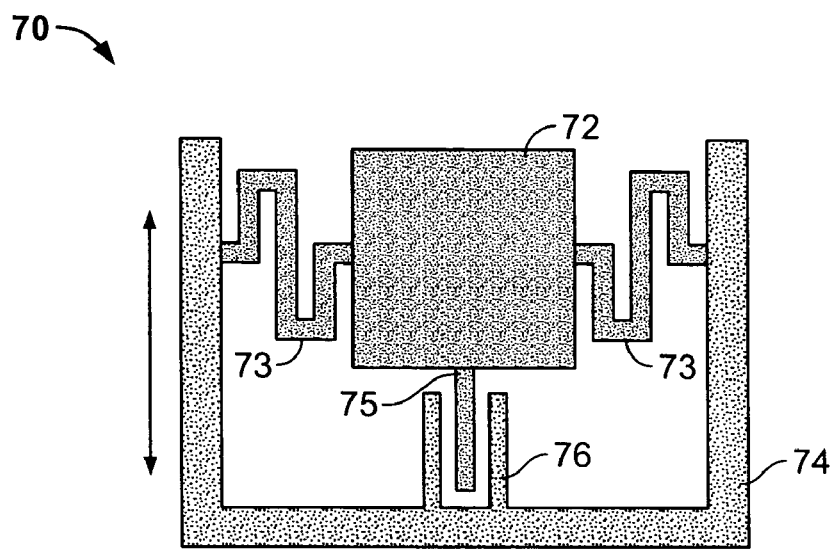
FIG. 6 is a diagrammatic view of an accelerometer construct useful with the inventive medical device of the present invention.

FIG. 6 depicts an accelerometer 70 in accordance with one embodiment of the present invention. The accelerometer 70 may be incorporated in a medical device for the purpose of monitoring patient vital signs such as pressure, pulse or flow. Accelerometer 70 consists generally of a stationary element 74 which may be part of or affixed to a structural element in the medical device and a moveable element 72. The moveable element 72 is suspended within the stationary element 74 by spring elements 73 which permits relative movement of the moveable element 72. A first projection 75 from the moveable element 72 interlaces with second projections 76 on the stationary element 74 such that movement of the first projection 75 within the second projections 76 induces a current within the stationary element 74. The relative strength of the induced current is then correlated to the pressure on the moveable element 72 and indicative of the stimulus being sensed.

Figure 7:
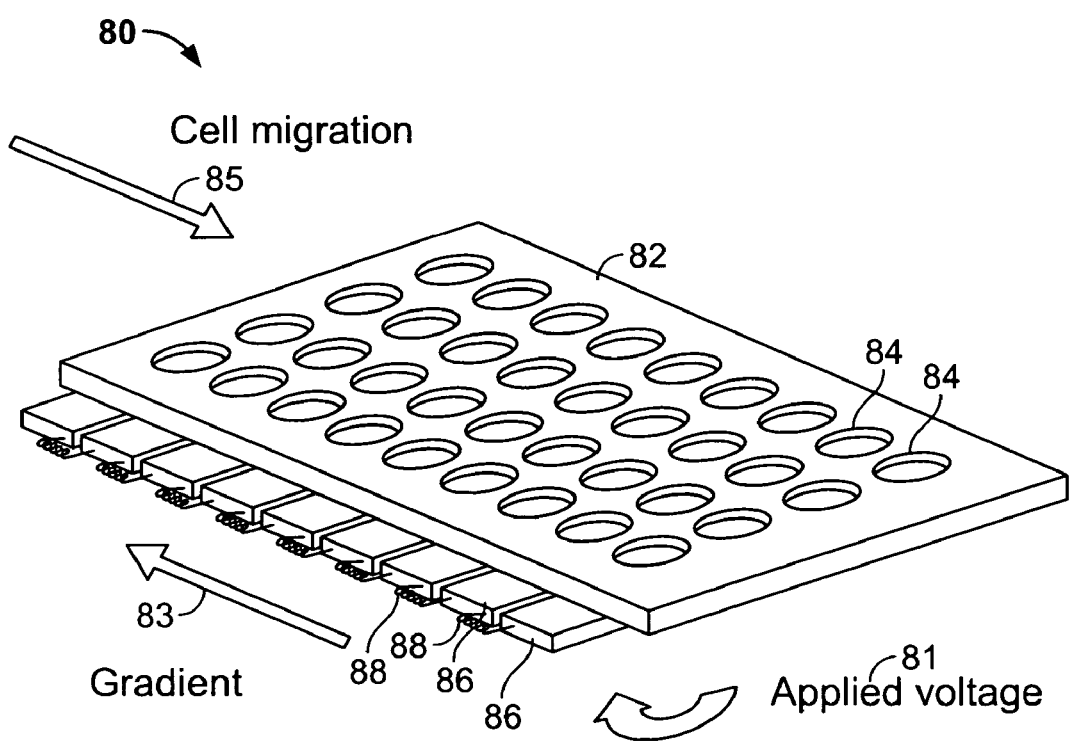
FIG. 7 is a fragmentary perspective view of an embodiment of the inventive medical device of the present invention depicting a galvanotactic construct for stimulating endothelial cell attachment and proliferation along the surface of the inventive medical device.

An embodiment of the inventive medical device employing a galvanotactic field gradient 80 is depicted in FIG. 7. In accordance with this embodiment of the invention, there is provided a galvanotactic stent in which the stent material is at least partially fabricated by multi-layer physical vapor deposition. A first substrate layer is deposited, then a conductive layer is deposited and interdigitated electrodes formed in the conductive layer, with adjacent electrodes being separated by dielectric material, a final top insulating layer is deposited and a plurality of openings formed and patterned to match the position of the interdigitated electrodes in the intermediate conductive layer. Upon application of an electrical current to the device, the interdigitated electrodes become charged and a focused current emanates from the openings in the top insulating layer and is patterned in correspondence with the pattern of openings in the top layer.

A suitable power sources may be an externally applied RF source that induces resonator circuitry in the stent to charge a solid state capacitor formed in the stent, thus providing an integrated power supply within the stent to maintain a charge source for the interdigitated electrodes.

Since it is known that endothelial cells migrate under the influence of an applied field, the presence of an electrical field integral with the stent is expected to enhance endothelialization of the stent surfaces and promote the formation of healthy neointimal tissue, while lowering the incidence of restenosis associated with stent implantation.

Thus, by forming a plurality of openings 84 in an arrayed pattern in a structural element 82 of a medical device, and providing an array of electrodes 86 electrically connected 88 to one another in adjacent proximity to the plurality of openings 84, then applying a voltage 81 to the electrodes 86, an electrical field gradient 83 is created along the pathway of endothelial cell migration 85 across the structural surface 82 of the medical device. Thus, the applied electrical field gradient 83 may be employed in conjunction with a medical device, such as a stent, to preferentially enhance endothelial cell binding and migration to provide surface coverage and healing of the device.

Figures 10, 11:
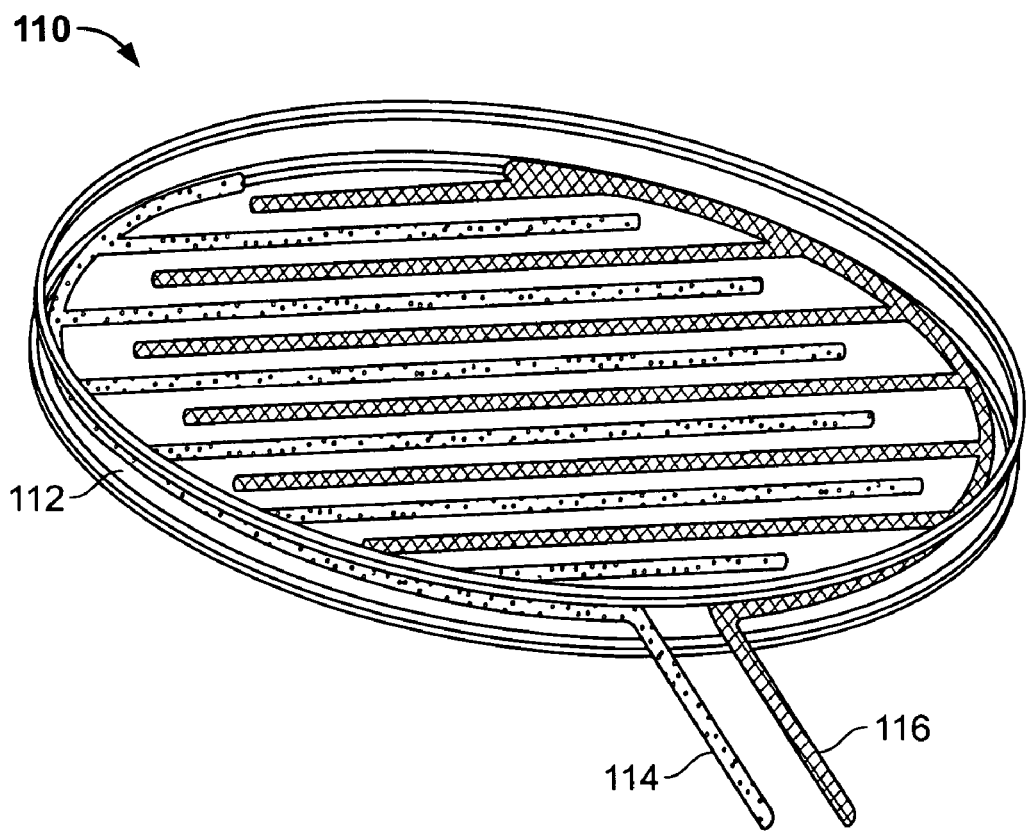
FIG. 10 is a table illustrating the relationship of specificity of MEMs device functionality and the type of functionality applicable based upon a range of specificity.
FIG. 11 is a diagrammatic perspective view of an embodiment of the present invention employing impedance spectroscopy as the functional approach.

FIG. 10 differentiates different approaches to biosensing based upon their sensitivity, with impedance spectroscopy having a low sensitivity and receptor/ion-channel completing having a high sensitivity. Thus, an endoluminal stent may include a conductive polymer with a biological element, such as a lipid, that forms an embedded circuit in the stent that responds to changes in a physiological condition in the body and produces a change in conductivity in known relationship with the change in the physiological condition. Examples of this type of mechanism of action are conductive polymers such as polypyroles and polypyrolidones used as artificial tongues in the food industry. FIG. 11 depicts a representative type of spectroscopic device 110. An example of a device 110 suitable for impedance spectroscopy using composite films of conductive polymers and lipids in a membrane is illustrated in FIG. 11. A conductive polymer membrane 112 encloses a first electrode 114 and a second electrode 116 which are interlaced relative to one another. Binding of an external component to the polymer membrane 112 causes an impedance change in the voltage between the first and second electrodes 112, 116 which is detectable by impedance spectroscopy.

Figure 12:
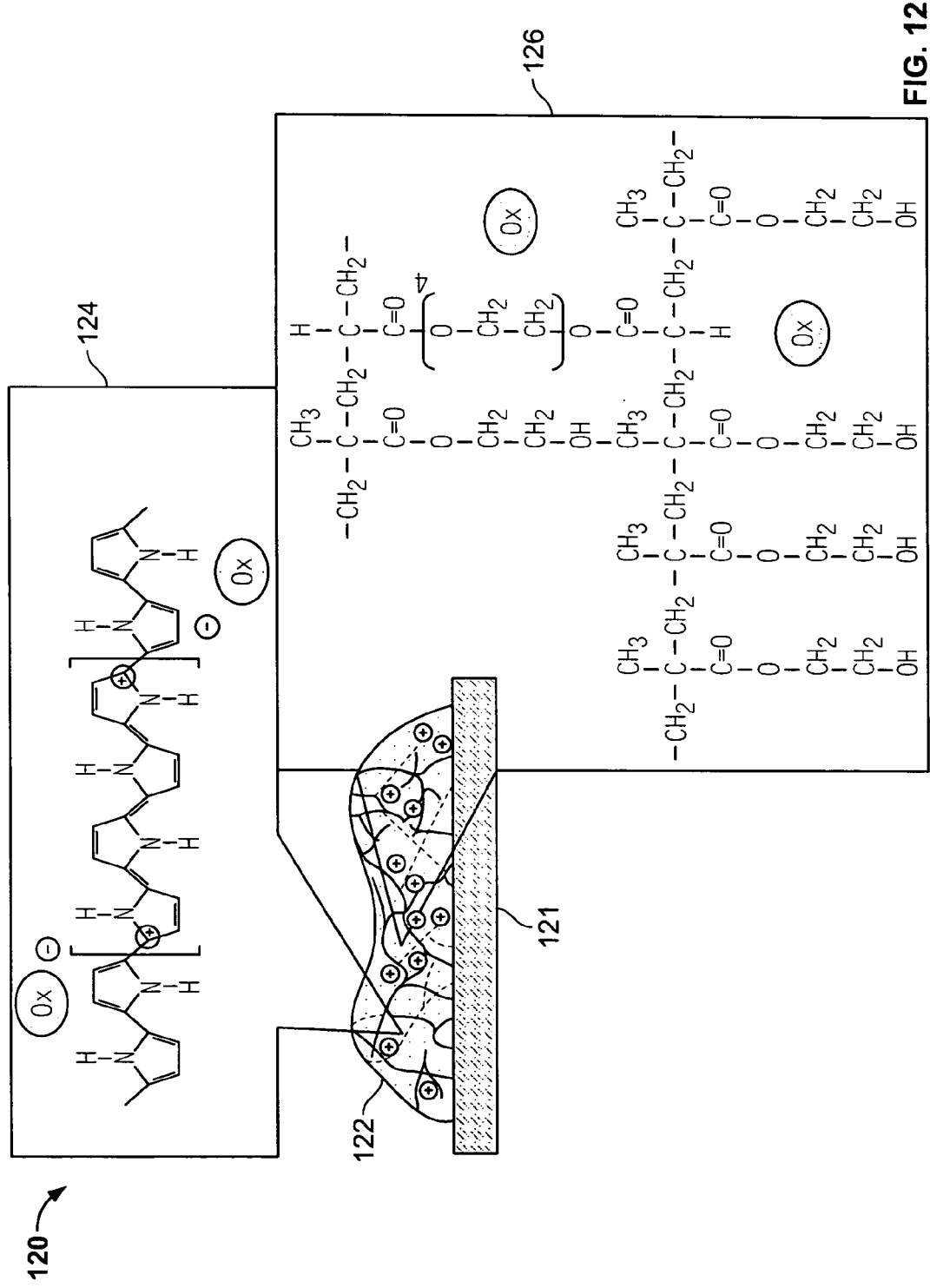
FIG. 12 is a diagrammatic view of an embodiment of the present invention employing amperometric measurement by peroxide generation in a composite bioactive hydrogel membrane.

Another aspect of the invention is that conductive polymers on a stent may be a device 120 for amperometric measurement by oxidase binding that generates peroxides to yield free electrons and provides detectable signal from the sensor device as depicted in FIG. 12. Thus, polyHEMA (polyhydroxyethyl methacrylate) 126 or polyethylene glycol may be used as the hydrogel matrix with polypyrole in combination with enzyme as a counteranion, may be employed. The conductive polymers may be coated onto stents or other medical devices to sense chemical moiety binding, such as blood glucose, and produce an amperometric measurement indicative of the chemical moiety binding.

Figure 13B:
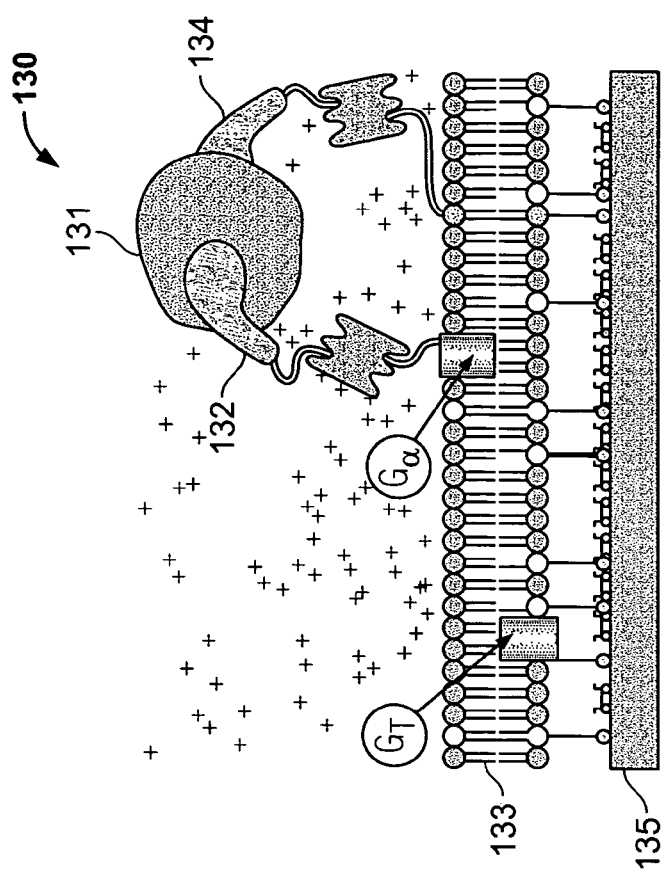
FIG. 13 (A–B) is a diagrammatic view of an embodiment of the present invention employing an antibody/ion-channel switch as a synthetic biosensor.
Figure 13A:
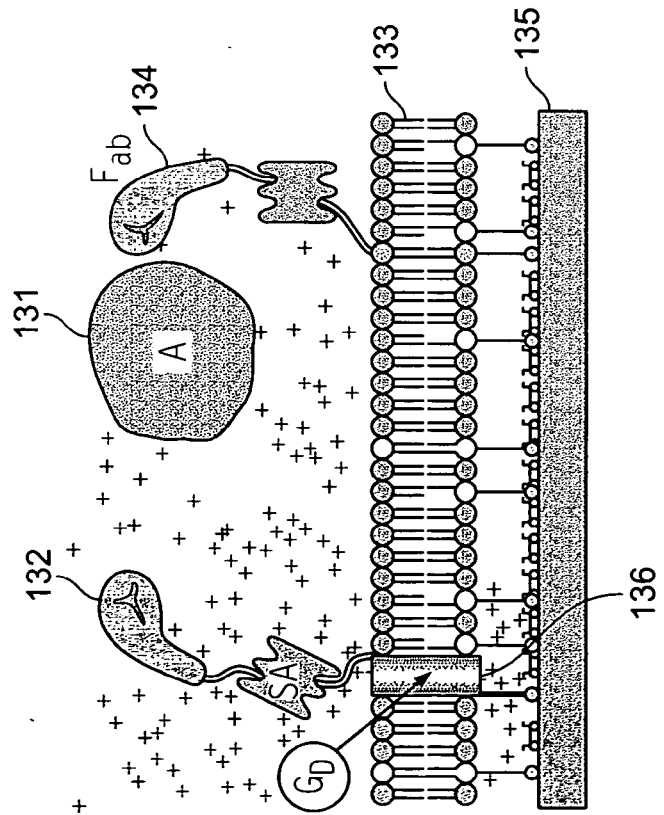

Alternatively, voltage generated by ion channel activity from receptor binding mediated events may be employed to generate a voltage signal for a stent-based sensor 130, as illustrated in FIGS. 13A and 13B. Immobilized ion channels (GT), synthetic archaebacterial membrane spanning lipids and half-membrane-spanning tethered lipids are attached to a conductive surface via polar linkers and sulphur bonds. Polar spacer molecules are directly attached to the conductive surface using the same chemistry. Mobile half-membrane-spanning lipids and mobile ion channels (Ga) complete the membrane. The mobile ion channels are biotinylated and coupled to biotinylated antibody fragments Fab9 132, 134 using streptavidin (SA) intermediates. Some of the membrane spanning lipids possess biotin-tethered Fab9 132, 134. In the absence of analyte (A), the mobile ion channels diffuse within the outer monolayer of the tethered membrane, intermittently forming conducting dimers (GD). The addition of the targeted analyte crosslinks the Fabs on the lipids and Ga and forms complexes that tether the Ga distant from their immobilized inner-layer partners. This prevents the formation of channel dimers and lowers the electrical conductivity of the membrane.

Figure 14:
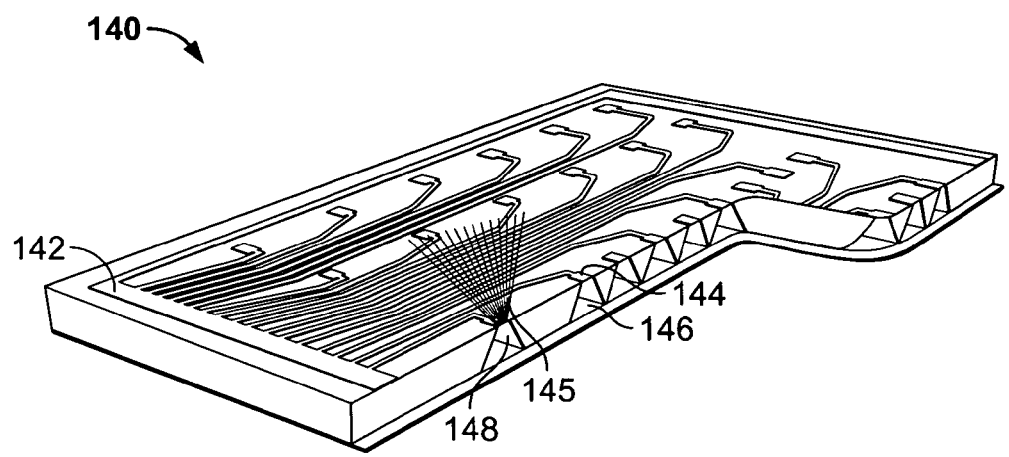
FIG. 14 is a perspective, partial cut-away view of an embodiment of the present invention employing electrocorrosion to release a bioactive agent.

FIG. 14 illustrates a type of drug delivery mechanism that functions by electrocorrosion 140 and may be incorporated into an implantable medical device, such as a stent. The device consists generally of a conductive metal foil 142 forming a cap 144 over a reservoir 148 containing a bioactive agent. The entire assembly is formed onto a surface of a medical device which may act as a sealing layer 146 to retain the bioactive agent. Upon application of an electrical field to the conductive metal foil 142, the cap 144 will corrode at a known rate and emit a flow 145 of the bioactive agent after the cap has corroded. Thus, controlled drug elution may be accomplished employing the electrocorrosion mediated drug delivery device 140 of the present invention.

Figure 15A:
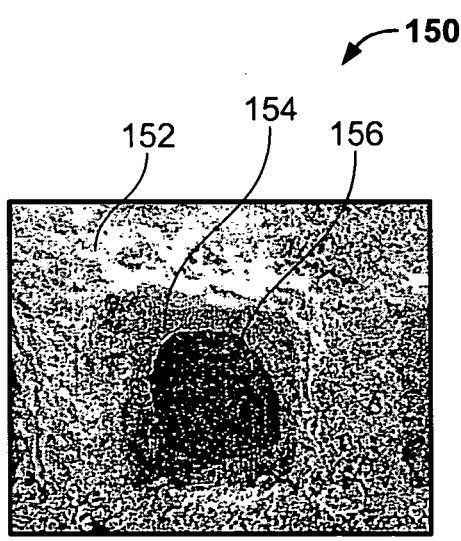
FIG. 15A is a photomicrograph depicting a MEMs device forming an artificial muscle valve, in an open position, to regulate release of a bioactive agent, in accordance with an alternative embodiment of the present invention.
Figure 15B:
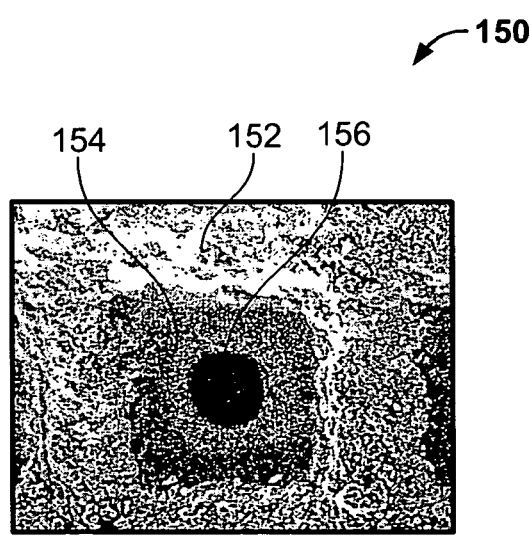
FIG. 15B is a photomicrograph depicting a MEMs device forming an artificial muscle valve, in a closed position, to regulate release of a bioactive agent, in accordance with an alternative embodiment of the present invention.

FIGS. 15A and 15B depict a first closed state and a first open state, respectively, of a microvalve 150. The microvalve 150 consists generally of a scaffold 152 which may be coated with polyHEMA, an actuatable microvalve 154 which functions as a variable opening to control passage of fluids, such as bioactive agents through the microvalve 154. The microvalve 154 may be fabricated from shape memory materials or conductive polymers, such as polyanaline. The microvalves 150 are preferably provided in an array and associated with drug-eluting reservoirs formed in structural elements of a medical device.

Figure 16A:
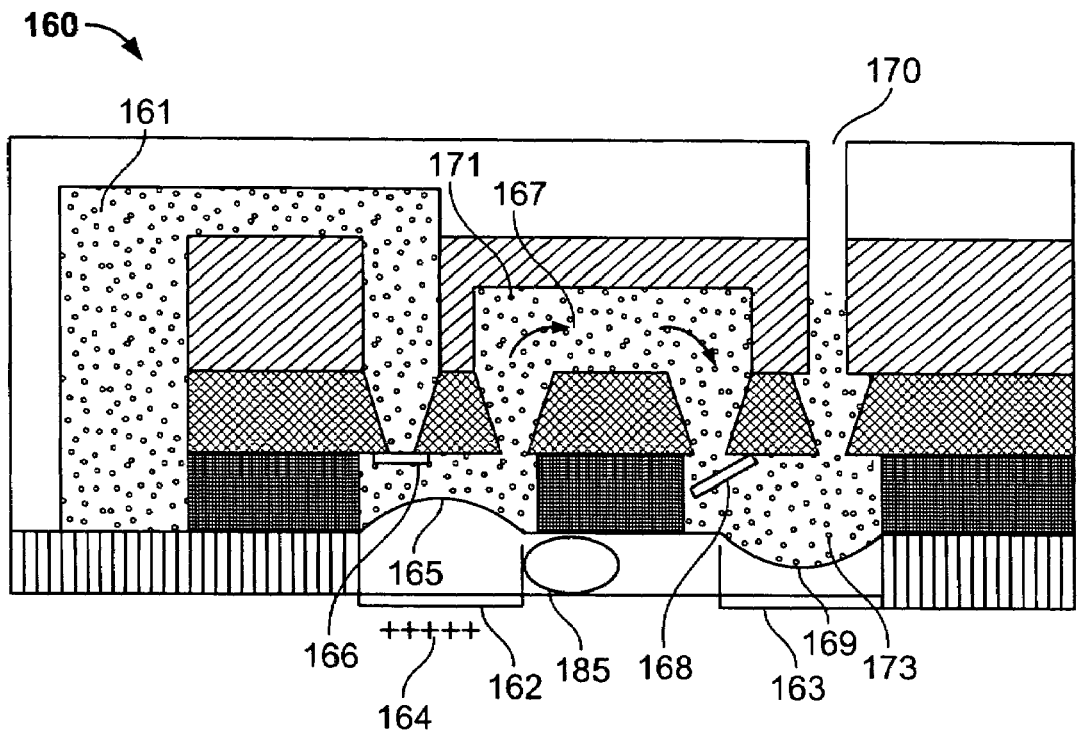
FIG. 16A is a diagrammatic cross-sectional view of a continuous electro-wetting micropump in accordance with an alternative embodiment of the MEMs functional medical device of the present invention, depicting the micropump in a loading state.
Figure 16B:
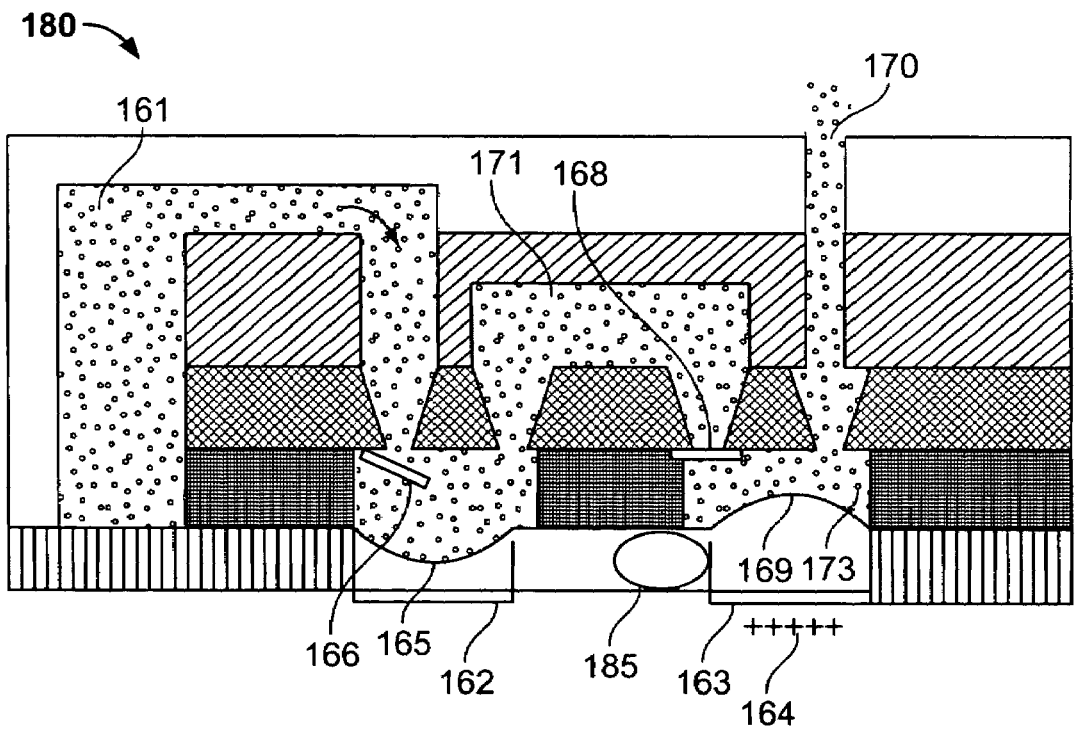
FIG. 16B is a diagrammatic cross-sectional view of a continuous electro-wetting micropump in accordance with an alternative embodiment of the MEMs functional medical device of the present invention, depicting the micropump in a loading state.
Figure 17A:
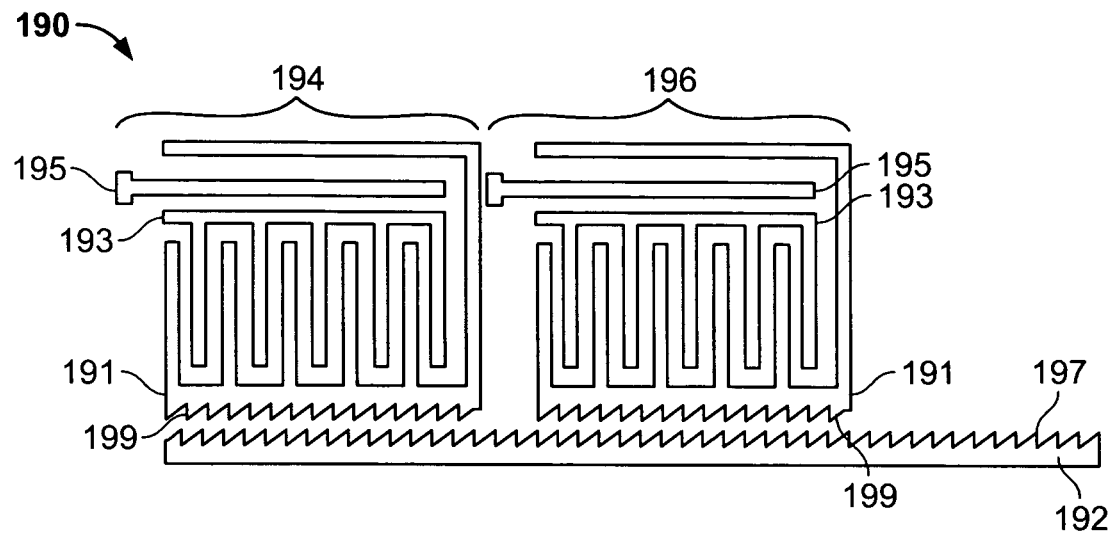
FIGS. 17A–17D are sequential fragmentary diagrammatic views depicting an actuating stent having micromotors and actuating rails for expanding the stent and the process of actuating the micromotors and moving the actuating rails.
Figure 17B:
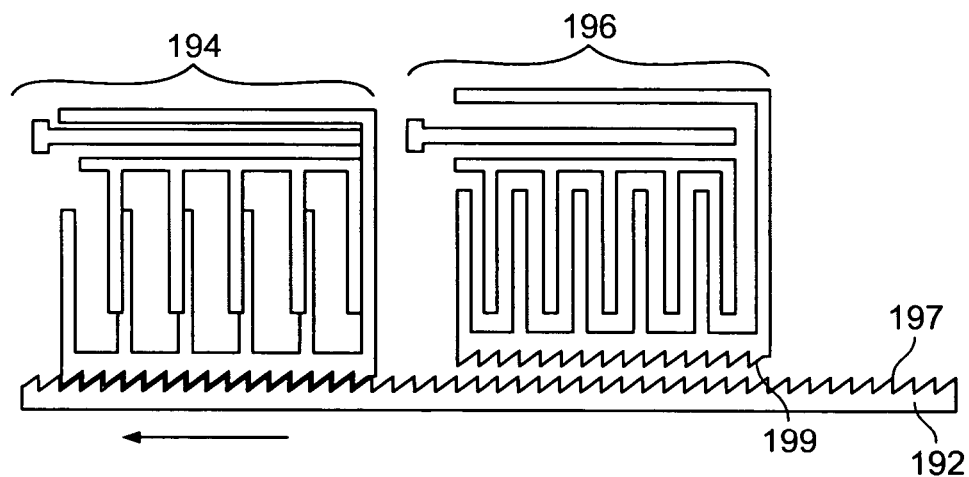
Figure 17C:
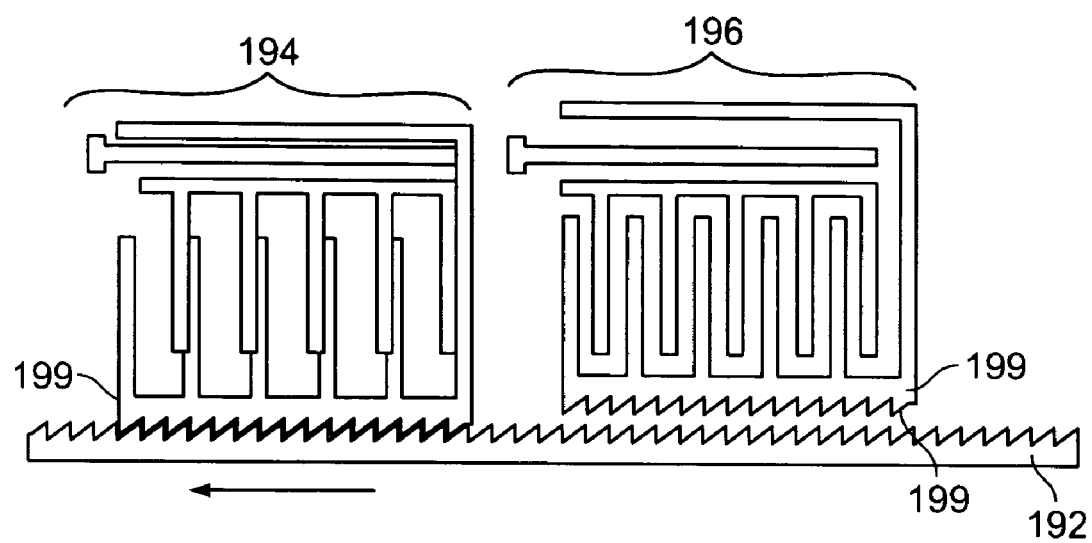
Figure 17D:
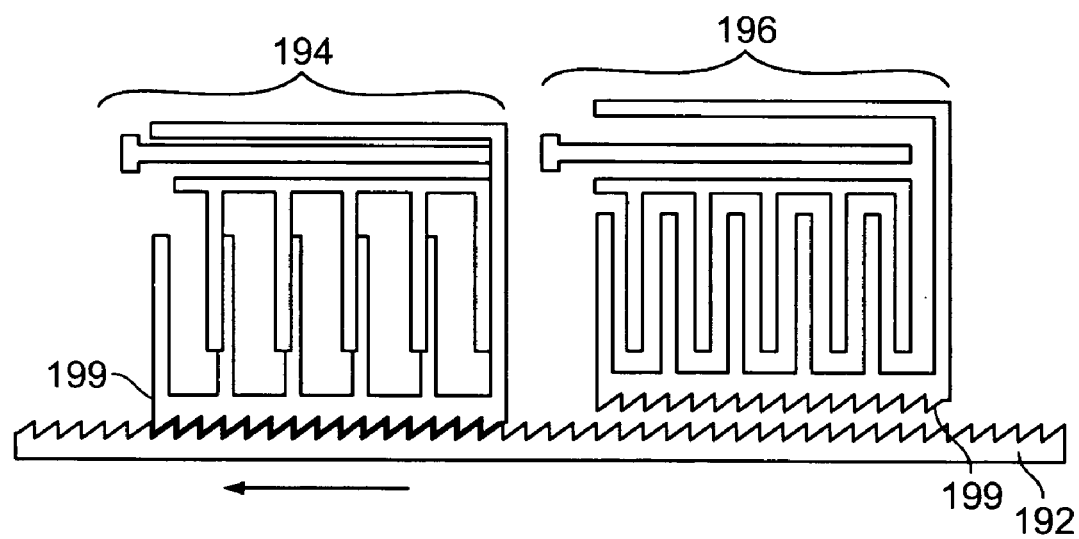

FIGS. 16A and 16B depict an electrowetting micropump 160 in which a nanofabricated or microfabricated fluid flow pathway is formed between structures. A first reservoir 161 terminates with a first gate valve 166 which permits or restricts fluid flow between the first reservoir 161 and a second reservoir 173. An electrolytic pump 185 drives a first diaphragm 165 which is communication with the second reservoir 173, to close the first gate valve 166, and pulls a second diaphragm 169, which opens a second gate valve 168 to drive fluid from the second reservoir 173 to a third reservoir 173. The electrolytic pump 185 is driven by electrowetting of a first membrane 162 on the first gate valve 16 side of the pump. By switching to electrowetting of a second membrane 163, as depicted in FIG. 16B, fluid within the third reservoir 173 is emitted from an exit opening 170 by actuation of the second diaphragm 169.

For each of the types of inventive microsensor devices contemplated by the present invention, it is necessary to have an external means for interrogating the microsensor device to determine its state. Transcutaneously applied RF energy is preferably employed to interrogate the inventive microsensor devices, or cause the inventive microsensor devices to actuate for either drug delivery or micromachine actuation. There is an exponential relationship between frequency and data density that may be transmitted over a given frequency is known in the art. Similarly, there is an inverse relationship between frequency and range. See, e.g., FIG. 3 and Leeper, D. G., Scientific American, May 2002, which is hereby incorporated by reference. In the ultrawideband frequency, large gigabyte level data densities may be obtained, but over relatively short distances of a few meters. It is contemplated that in the present invention, at terahertz frequencies it is expected that higher data densities may be obtained even while sacrificing range. Since a range of only a few centimeters is required to transcutaneously interrogate an implanted medical device, very high frequencies in the terahertz range may be employed with the concomitant effect of yielding terabyte data densities that are expected to yield sufficient data streams to construct realtime 3D images representative of the condition of the implanted microsensor medical device.

Figure 18A:
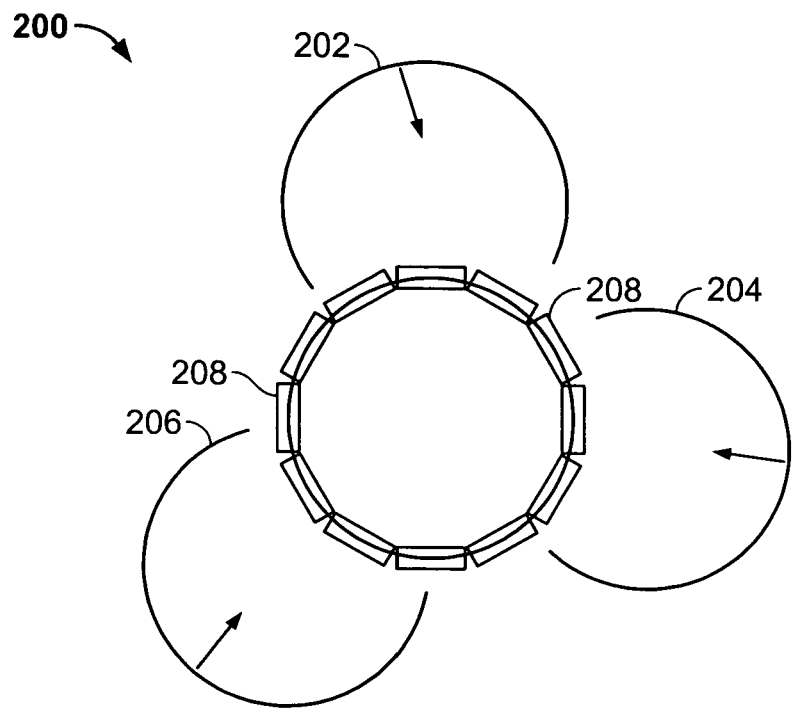
FIG. 18A is an exploded diagrammatic view of the inventive actuating stent.
Figure 18B:
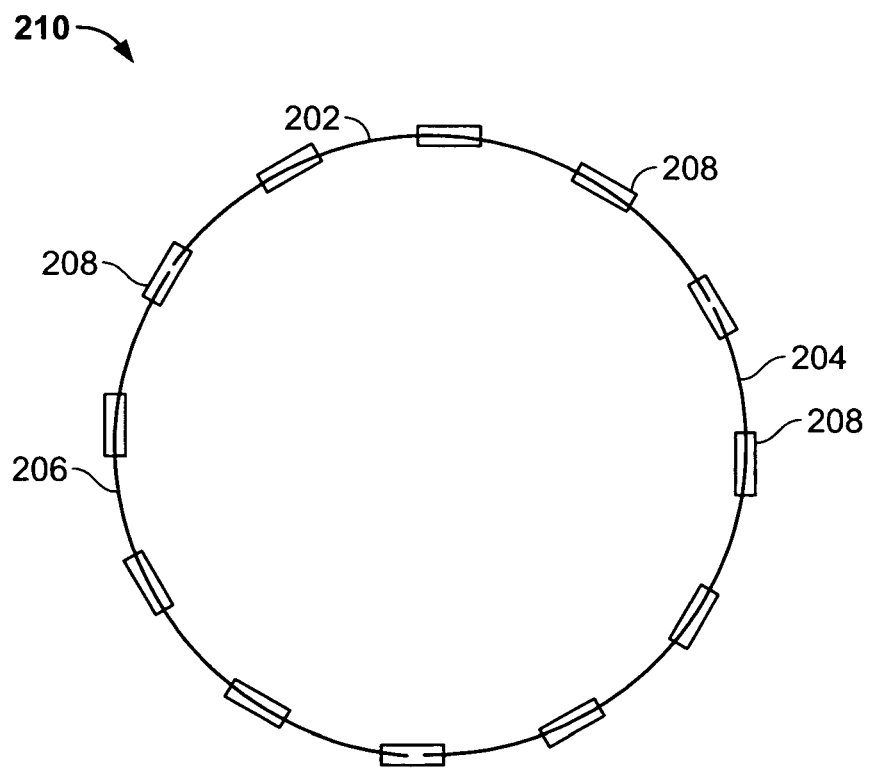
FIG. 18B is a diagrammatic view of the inventive actuating stent in its fully diametrically expanded state.

As noted above, stent based actuators may have the basic elements of a power generator, logic circuit, communications module and an actuator assembly as depicted in FIG. 5. A particular embodiment of a stent actuator capable of enlarging the diameter of the stent is illustrated in FIGS. 17A–17D and 18A and 18B, in which a linear micromotor having at least two cooperating elements 194, 196 is employed in conjunction with a drive track 192 associated with at least one arcuate section of a stent 202, 204 or 206 to axially drive the arcuate stent sections 202, 204, 206, thereby diametrically expanding the stent as depicted in FIG. 18B. A stent may be fabricated of a plurality of micromotors and a plurality of curved tracks, it being understood that each curved track is generally linear in nanoscale. Each of the micromotors 194, 196 are configured as "inchworm" type devices, in which there are first 191 and second 193 interlacing comb members, each of the first 191 and second 193 comb members are electromechanically coupled to a contact 195 which drives relative movement of one of the first 191 or second 193 comb members relative to one another. A first comb member 191 has a plurality of projections 199 extending therefrom which engage a mating plurality of projections 192 on the drive track 192 associated with the stent sections 202, 204 or 206. In operation, an electrical signal transmitted through the contact 195 drives a first comb member 191 toward the contact, thereby displacing the comb member 191 toward the drive track 192 and toward the second comb member 193, whereupon the projections 199 on the first comb member mate with the projections 197 on the drive track. Another electrical signal applied to the contact 195, then drives causes the second comb member 193 to displace, thereby moving the first comb member 191 and the drive track 192 axially relative to the drive track 192. An adjacent micromotor 196 undergoes sequentially identical steps in step-wise fashion to axially move the drive track 192 in an "inchworm" fashion.

While the present invention has been described with reference to its preferred embodiments, those of ordinary skill in the art will understand and appreciate that variations in device design, device selection, design of the MEMs device integral with the implantable medical device, and the functionality of the MEMs device may be made without departing from the scope of the invention.

What is claimed is:

1. An endoluminal stent having a plurality of structural elements defining luminal and abluminal wall surfaces thereof, a central lumen, and a plurality of openings passing through the luminal and abluminal wall surfaces, comprising at least one microelectromechanical system operably associated with at least one of the plurality of structural elements, wherein the plurality of structural elements further comprise a plurality of arcuate members having a plurality of first projections, wherein the stent further comprises a plurality of micromotors operably associated with each of the plurality of arcuate members, each of the plurality of micromotors having at least one drive element having a plurality of second projections, the plurality of second projections interfacing with at least some of the plurality of first projections, whereby actuation of the plurality of micromotors causes the at least one drive element to engage at least some of the plurality of second projections with at least some of the plurality of first projections on at least one of the plurality of arcuate members and axially displace the at least one of a plurality of arcuate members.

2. The endoluminal stent according to claim 1, wherein each of the plurality of micromotors further comprises at least two interlacing comb members.

3. The endoluminal stent according to claim 2, wherein the at least two interlacing comb members are electrically associated with to at least one inductive member.

4. The endoluminal stent according to claim 1, wherein the stent further comprises a plurality of recesses in at least one of the plurality of structural members, each of the plurality of recesses further having at least one cantilever member projecting over an associated recess, wherein the at least one cantilever member is capable of oscillating upon application of an external energy thereto.

5. The endoluminal stent according to claim 4, wherein each of at least one cantilever member further comprises a piezoelectric element.

6. The endoluminal stent according to claim 4, wherein binding of at least one of cellular and sub-cellular components to the at least one cantilever member sufficiently attenuates is capability to oscillate upon application of an external energy thereto, such that interrogation of the oscillation returns a signal representative of the attenuated oscillation.

7. The endoluminal stent according to claim 6, wherein the interrogation of the oscillation occurs at an ultrawideband frequency.

8. The endoluminal stent according to claim 1, further comprising a plurality of openings passing through at some of the plurality of structural elements and a plurality of electrodes electrically coupled to one another and positioned proximate the plurality of opening to impart an electrical field gradient across the plurality of openings when a voltage is applied to the plurality of electrodes.

9. A system for actuating the endoluminal stent of claim 1, comprising at least one actuator member operably associated with the endoluminal stent, at least one communication circuit in operably communicating with the at least one actuator member, at least one logic circuit electrically coupled to the communication circuit, and at least one power source.

10. The system for actuating the endoluminal stent according to claim 9, wherein the at least one actuator member further comprises at least two interlacing comb members, each of the at least two comb members being operably coupled to a contact, and having a plurality of drive projections for interfacing with a structural member of the endoluminal stent.

11. The system for actuating the endoluminal stent according to claim 10, wherein the contact is in operable communication with the communication circuit.

12. The system for actuating the endoluminal stent according to claim 9, wherein the at least one power source further comprises an external power source which is inductively coupled to the at least one actuator member.

13. The endoluminal stent according to claim 1, wherein the at least one system is selected from the group of cantilevers, nanothermometers, accelerometers, galvanotactic assemblies, impedance spectrometers, amperometric measurement, antibody/ion-channel sensors, electrocorrosive sensors, microvalves, micropumps, micromotors, microactuator and drive assemblies.

* * * * *

UNITED STATES PATENT AND TRADEMARK OFFICE
CERTIFICATE OF CORRECTION

PATENT NO. : 7,235,098 B2  Page 1 of 1
APPLICATION NO. : 10/945203
DATED : June 26, 2007
INVENTOR(S) : Julio C. Palmaz It is certified that error appears in the above-identified patent and that said Letters Patent is hereby corrected as shown below:

Title page Item [56]
Page 2 - OTHER PUBLICATIONS:
 Please insert -- "Microdevices in Medicine" by Polla, D.L., et al., Annual Rev. Biomed. Eng., Vol. 2, pp. 551-576 (2000) --

Title page Item [56]
Page 2 - OTHER PUBLICATIONS
 Please insert -- "Microactuators toward microvalves for responsive controlled drug delivery" by Low, L.M., et al., Sensors and Actuators, Vol. B67, pp. 149-160 (2000) --

Column 1 - Line 37:
 Please delete "*Actuator*," and insert -- *Actuators*, --

Column 2 - Line 66:
 Please delete "microsensor" and insert -- Microsensor --

Column 5 - Line 29:
 Please delete "a" and insert -- as --

Column 5 - Line 43:
 Please delete "an" and insert -- a --

Signed and Sealed this

Twentieth Day of November, 2007

JON W. DUDAS
*Director of the United States Patent and Trademark Office*